United States Patent [19]
Andre et al.

[11] Patent Number: 5,071,985
[45] Date of Patent: Dec. 10, 1991

[54] PROCESS FOR THE PREPARATION OF MORPHINANE DERIVATIVES

[75] Inventors: Jean-Daniel Andre, des Combes; Jean-Robert Dormoy, nue du Thor; Alain Heymes, Frédéric Mistral, all of France

[73] Assignee: Sanofi, Paris, France

[21] Appl. No.: 406,248

[22] Filed: Sep. 12, 1989

[30] Foreign Application Priority Data

Sep. 13, 1988 [FR] France .................................. 88 11930

[51] Int. Cl.$^5$ ............................................ C07D 489/08
[52] U.S. Cl. ............................................ 546/45; 546/44
[58] Field of Search .................................. 546/44, 45

[56] References Cited

U.S. PATENT DOCUMENTS 4,265,890  5/1981  Holden et al. ...................... 514/213
4,707,483  11/1987  Bondinell et al. ................... 514/273

OTHER PUBLICATIONS

Kiso et al., Chemical Abstracts, vol. 92: 198745n (1980).
Irie et al., Chemical Abstracts, vol. 93: 186623d (1980).
Bentley, "The Chemistry of the Morphine Alkaloids", Oxford, at the Clarendon Press, 1954, pp. 60, 406, and 413.

Primary Examiner—Diana G. Rivers
Attorney, Agent, or Firm—Wegner, Cantor, Mueller & Player

[57] ABSTRACT

The invention relates to a process for the preparation of morphinane derivatives of general formula:

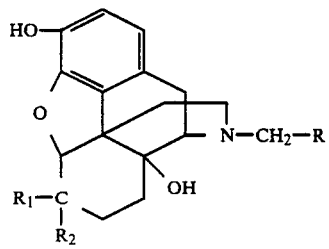

I by demethylation of 3-methoxylated compound with a sulfonic acid selected from methanesulfonic acid and trifluoromethanesulfonic acid in the presence of a sulfide.

14 Claims, No Drawings

PROCESS FOR THE PREPARATION OF MORPHINANE DERIVATIVES

The present invention relates, in a general manner, to a novel process for the preparation of morphinane derivatives.

In particular, the invention relates to a novel process for the preparation of morphinane derivatives of general formula:

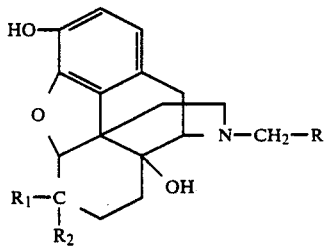

I in which R is selected from hydrogen, $C_1$–$C_4$ alkyl, $C_3$–$C_4$ cycloalkyl, $C_2$–$C_4$ alkenyl or $C_2$–$C_4$ alkynyl, $R_1$ is hydrogen, $R_2$ is hydroxyl or $R_1$ and $R_2$ form together with the carbon atom to which they are attached the C=O group,
as well as their pharmaceutically acceptable salts.

Thus, the process of the invention makes possible, in particular, the preparation of naloxone (R is vinyl, $CR_1R_2$ is C=O), nalmexone (R is 2-methyl 1-propenyl, $CR_1R_2$ is C=O) or naltrexone (R is cyclopropyl, $CR_1R_2$ is C=O) or nalbuphine (R is cyclobutyl, $R_1$ is H and $R_2$ is OH), these compounds being widely known for their antagonistic properties to narcotics, as well as the preparation of oxymorphone, a compound used for its analgesic properties.

Among the compounds of formula I those in which R is selected from hydrogen or vinyl or cyclopropyl and $CR_1R_2$ is the C=O group constitute preferred compounds.

Furthermore, the invention relates preferentially to the preparation of the compound of formula I in which R is hydrogen and $CR_1R_2$ is C=O as well as the compound of formula I in which R is vinyl and $CR_1R_2$ is the C=O group.

For the last 10 years boron tribromide has been the reagent of choice for the demethylation of the methyl ether situated at position 3 of many morphine derivatives comprising the skeleton:

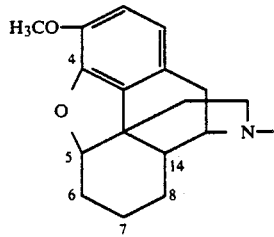

Ia in particular the derivatives comprising a hydroxyl group at position 14.

This reagent exhibits, in fact, great selectivity and can be used under mild conditions. Even though the use of boron tribromide tends to become more and more generalized for this type of reaction, the latter does however present certain problems on an industrial scale on account of its toxicity, its highly corrosive nature and the difficulty in handling it.

The search for an industrial process enabling these disadvantages to be eliminated thus remains of paramount importance. However, the choice of another reagent suitable for bringing about the demethylation of the methyl ether of compounds of structure Ia proves to be difficult.

It is well known that the family of the morphinane alkaloids require a special chemical approach on account of their complex structure. The demethylation at position 3 is no exception to this rule all the more so since the carbons 6, 7 and 14 may be functionalized and/or may be implicated in carbon-carbon bonds, which may be double bonds.

As a consequence, a reagent capable of brining about this demethylation must show great selectivity between the two ether functions borne by the carbons 3 and 4 and leave intact the other functions possible present (ketones, alkenes, alcohols ... ).

For these reasons, each family or morphine derivatives of structure Ia, for example, oxycodone, codeine, thebaine and their respective analogues, in practice has its own appropriate reagent, boron tribromide being, however, the one which appears to be the most common to these different families.

Consequently, the application of a reaction already known to bring about the demethylation of methyl ethers in general can certainly not be considered as being applicable with certainty to the morphinanes of structure Ia.

In this connection, the demethylation of compounds of relatively simple structure by means of a couple sulfonic acid/derivative of the sulfide type, for instance methanesulfonic acid or trifluoromethanesulfonic acid and methionine, is known. This method is reported in particular in J. C. S. Perkin I. pp. 2288–2289 (1977). The results obtained with this method are usually very varied (yield of demethylated compounds varies from 30 to 90%) and may be poor. This is the case for p-methoxyacetophenone: no reaction is recorded at 20° C. and only 30% yield of p-hydroxyacetophenone is obtained after 72 hours at 60° C.

In conclusion, the generalization of this method cannot be contemplated in the light of the known results, less still when it is a question of its application to compounds of complex structure.

It has nonetheless been found that the process in question can be used satisfactorily for the demethylation of certain derivatives of morphinane comprising structure Ia, namely the compounds of formula II below, whereas it has proved totally ineffective for the demethylation of other families of morphine derivatives of similar structure.

Thus, surprisingly, it has been possible to demonstrate that the demethylation reaction in question can be applied effectively and selectively to the demethylation of compounds of structure Ia comprising a hydroxyl group at position 14 and a hydroxyl group or ketone group at position 6 with a view to forming the compounds of formula I.

Consequently, the present invention relates to a process for the preparation of compounds of formula I, comprising reacting an equivalent of a morphine derivative of general formula:

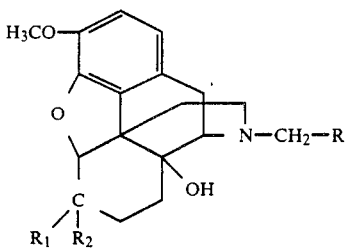

in which R, $R_1$ and $R_2$ are as defined previously, with 5 to 50 equivalents of a sulfonic acid selected from methanesulfonic acid and trifluoromethanesulfonic acid in the presence of 1 to 5 equivalents of a sulfide of general formula:

$$W-S-W_1 \quad\quad III$$

in which W and $W_1$, which are identical or different, each is a $C_1$-$C_4$ linear alkyl radical, for example n-butyl, the W group being optionally substituted with one amino and one carboxyl, or W and $W_1$ may form with the sulfur atom a saturated ring with up to 8 carbon atoms, for example, a tetrahydrothiophenyl group.

When W is substituted with one amino and one carboxyl group, the compound of formula II is an amino acid comprising a sulfur function. Such an amino acid is preferably methionine.

The morphine derivatives of formula II are known compounds which have been described in particular in the U.S. Pat. Nos. 4,141,897, 4,161,597 and 4,667,037 and also in Chem. Abst. 104, 6055, 98, 204267 and 75, 107912.

The reaction usually takes place in the presence of a large excess of sulfonic acid, preferably from 25 to 35 equivalents whereas a slight excess of sulfide of formula III is sufficient, i.e. from 1 to 2 equivalents.

In most cases, the reaction temperature varies from 20° to 60° C. and may be raised to a maximum of 80° C.: it is preferably between 30° C. and 40° C.

In fact, above 60° C., and depending on the compound, degradation of the final demethylated product begins to be detectable.

Without being limiting, the following operating conditions are usually used:

30 equivalents of sulfonic acid
1.5 equivalent of sulfide of formula III per equivalent of compound of formula II, the reaction being preferably carried out between 30° and 40° C. for about 15 hours.

After purification of the crude product thus obtained, the crystallization mother liquors contain in appreciable amount of the compound of formula I as well as of the compound of formula II which it is possible to recycle.

Other strong proton acids have been tested in the context of the process of the invention but have been found to be totally ineffective in bringing about the demethylation.

For example, it was not possible to form naloxone from N-allylnoroxycodone (formula II in which R is vinyl, $CR_1R_2$ is C=O) and 15 equivalents of chlorosulfonic acid or sulfuric acid and 1.5 equivalent of methionine during 1 to 8 h at 20° C. Similarly, the use of superacidic resins also leads to failure under the same conditions.

Furthermore, the process of the invention offers certain advantages in comparison with the demethylation process using boron tribromide. In the case, for example, of the formation of naloxone from N-allylnoroxycodone, the earlier process makes it possible to obtain a yield of about 62.5% into the final product. However, the treatment of the reaction mixture with a view to recovering the final product proves to be difficult to carry out in view of the large amounts of boron salts formed during the course of the reaction.

When it was also used for the demethylation of N-allylnoroxycodone, the process of the invention also produced naloxone in yields of about 63%. However, an approximately additional 10% of final product may be recovered from the recycling fluid. The recovery of the naloxone formed also appears to be easier because less emulsion is formed within the reaction mixture. Furthermore, the process of the invention proves to be more economical than the earlier process in view of the lower cost of the reagents used.

As mentioned previously, the process of the invention can be applied to the preparation of the compounds of formula I whereas it proves to be totally ineffective for the formation of morphine derivatives of similar structure.

To that effect, attempts at demethylation have been carried out on different compounds representing different families of different methoxylated morphine derivatives using the preferred reaction conditions according to the invention, namely 30 equivalents of methanesulfonic acid and 1.5 equivalent of methionine, the temperature and time of reaction being indicated below:

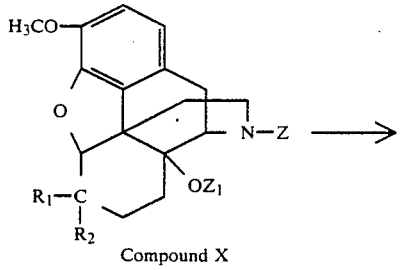

Compound X

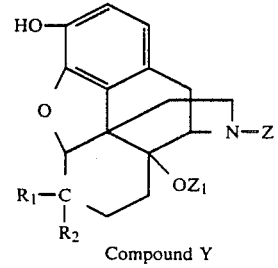

Compound Y a) Precursors of Naloxone

| Compound X | | | Time | | |
|---|---|---|---|---|---|
| Z | $CR_1R_2$ | $Z_1$ | T(°C.) | (h) | Results |
| $CH_3$ | C=O | $COCH_3$ | 20 | 12 | 59% of compound Y where $R_1$ = H |
|  |  |  | 40 | 7.5 | (L.C. and T.L.C.*) |
| $CO_2C_2H_5$ | C=O | $COCH_3$ | 20 | 20 | Complex mixture |
| H | C=O | H | 40 | 12 | 1% of corresponding |

-continued

| Compound X | | | Time | | |
|---|---|---|---|---|---|
| Z | CR₁R₂ | Z₁ | T(°C.) | (h) | Results |
| CO₂C₂H₅ | C=O | H | 20 | 48 | compound Y Complex mixture containing 18% of compound Y and 6% of compound X |

*L.C. = liquid chromatography
T.L.C. = thin layer chromatography b) Precursor of Naltrexone

| | | | 40 | 24 | complex mixture containing 15% of compound Y |
| | | | 20 | 6.5 | complex mixture containing 40% of compound Y | c) Precursor of Buprenorphine

The same process applied to the compound below:

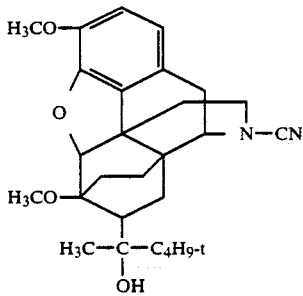

has shown that at 20° C. the reaction is very rapid and leads to a mixture of products. Analysis by nuclear magnetic resonance shows that demethylation has not taken place but that, on the other hand, the tertiary butyl group has not withstood the acid medium.

d) Precursor of Morphine

The process of the invention applied to codeine of formula:

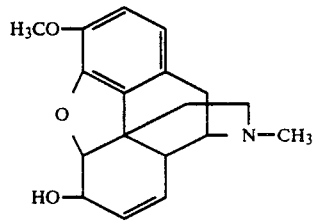

leads to a mixture of many products among which L.C. makes it possible to detect to the presence of morphine (about 10%), the starting material and a rearrangement product constituted by apocodeine.

e) Thebaine

The same type of reaction is carried out with thebaine of formula:

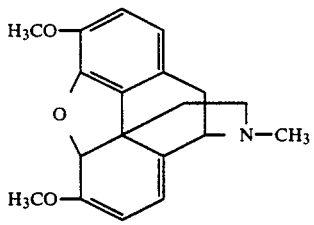

Initially, the process of the invention applied at 20° C. for 3 hours produces the rearranged product of formula:

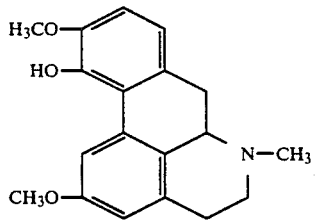

then a partial demethylation is observed which after 3 days at 20° C. leads to the derivative of formula:

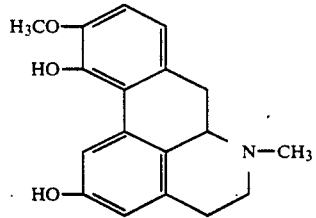

These negative results clearly show that the application of a demethylation process making use of methanesulfonic acid or trifluoromethanesulfonic acid and a sulfide of formula III is quite surprising in forming compounds of formula I.

The following non-limiting examples illustrate the process of the invention:

EXAMPLE 1

Preparation of 4,5-epoxy-3,14-dihydroxy-17-(2-propenyl)(5α) morphinan-6-one hydrochloride or naloxone a) Free base 34.12 g (0.1 mole) of 4,5-epoxy-14-hydroxy 3-methoxy-17-(2-propenyl)(5α)morphinan-6-one or N-allylnoroxycodone are added to 288 g (3 moles) of methanesulfonic acid. The dissolution is exothermic. 22.4 g (0.15 mole) of DL-methionine are added at 40° C. to the dark brown mixture obtained within 15 minutes. The reaction mixture is stirred at 40° C. for 15.5 hours, then is made alkaline with ammonia to pH=8 to 9. The mixture is extracted with ethyl acetate and 30.7 g of a crude product are obtained which are treated with alumina in chloroform solution. After recrystallization from chloroform, 19.8 g of naloxone are obtained (M.p.=177° C.), which represents a yield of 60%.

The crystallization mother liquors which contain 9% of naloxone and 12% of the starting material, respectively, with respect to the starting material used, are then recycled.

b) Hydrochloride 5 g of the purified base previously obtained are dissolved in 30 ml of warm acetone. After concentration to about 10 ml, 5 ml of 6N hydrochloric acid are added to the warm solution. The mixture is cooled to −10° C., the precipitate is filtered off, washed with acetone and dried at 50° C. in a vacuum.

4.83 g of naloxone hydrochloride are thus obtained. Yield: 87%.

EXAMPLE 2

Preparation of Naloxone 34.12 g (0.1 mole) of N-allylnoroxycodone are added to 288 g (3 moles) of methanesulfonic acid. 22.4 g (0.15 mole) of DL-methionine are added to the solution thus obtained at 30° C. during 15 minutes. The reaction mixture is stirred at 30° C. for 15.5 h, then it is made alkaline with ammonia to pH=8 to 9. The mixture is extracted with ethyl acetate and a chloroform solution of the crude product obtained is treated with alumina.

Naloxone is obtained in a yield of 60% after recrystallization from toluene (M.p.:176° C.).

The toluene mother liquors are recycled and in this way 7% of naloxone and 18% of the starting material with respect to the starting material used are recovered.

EXAMPLE 3

Preparation of Naloxone

A mixture of 3.41 g (0.01 mole) of N-allylnoroxycodone, 28.8 g (0.3 mole) of methanesulfonic acid and 2.19 g (0.015 mole) of di-n-butyl sulfide is stirred for 5 hours at 20° C., then for 14 hours at 40° C. and finally for 8 hours at 60° C.

The mixture is made alkaline with ammonia to pH=3 to 9, then is extracted with ethyl acetate. A chloroform solution of the product thus obtained is then treated with alumina and the product is recrystallized from toluene.

In this way, 1.64 g of naloxone are obtained, which represents a yield of 50%.

The crystallization mother liquors, which still contain about 9% of naloxone with respect to the starting material used, are then recycled.

EXAMPLE 4

Preparation of Naloxone

A mixture of 3.41 g (0.01 mole) of N-allylnoroxycodone, 28.8 g (0.3 mole) of methanesulfonic acid and 1.32 g (0.015 mole) of tetrahydrothiophene is stirred for 20 hours at 40° C. The mixture is made alkaline with ammonia to pH=8 to 9, then is extracted with ethyl acetate. A chloroform solution of the product thus obtained is then treated with alumina and the product is recrystallized from toluene.

In this way, 1.73 g of naloxone are obtained, which represents a yield of 53%. The crystallization mother liquors, which still contain 9 to 10% of naloxone with respect to the starting material used, are then recycled.

EXAMPLE 5

Preparation of Naloxone 1.7 g ($5.10^{-3}$ mole) of N-allylnoroxycodone are added to a mixture of 3.75 g ($25.10^{-3}$ mole) of trifluoromethanesulfonic acid, 1.12 g ($7.5.10^{-3}$ mole) of DL-methionine and 10 ml of trifluoroacetic acid.

The reaction mixture is stirred at 20° C. for 29 hours, then is made alkaline with ammonia to pH=8 to 9. It is extracted with ethyl acetate, then a chloroform solution of the product thus obtained is treated with alumina. After recrystallization from toluene, 1.15 g of naloxone are obtained, which represents a yield of 60%.

The crystallization mother liquors still contain 9% of naloxone with respect to the starting material used.

EXAMPLE 6

Preparation of 4,5-epoxy-3,14-dihydroxy-17-methyl(5α)morphinan-6-one or oxymorphone A mixture of 3.15 g ($10^{-2}$ mole) of 4,5-epoxy-14-hydroxy-3 methoxy-17-methyl(5α)morphinan-6-one or oxycodone, 28.3 g ($3.10^{-1}$ mole) of methanesulfonic acid and 2.2 g ($1.5.10^{-2}$ mole) of DL-methionine are heated to 40° C. The reaction mixture is stirred at this temperature for 12 hours and then poured onto ice. The mixture is made alkaline with ammonia to pH=8 to 9, then is extracted with dichloromethane. The organic phases are washed with water, dried over sodium sulfate and evaporated to dryness under reduced pressure. The crude product thus obtained (2.51 g) is purified on a column of silica by eluting with pure chloroform followed by a gradient with methanol.

2.17 g of oxymorphone are thus obtained, which represents a yield of 72%. M.p.:253° C.

Thin layer chromatography: Rf=0.60 (dichloromethane/methanol 7/3).

EXAMPLE 7

Preparation of 17-cyclopropylmethyl-4,5-epoxy-3,14-dihydroxy(5α)-morphinan-6-one or naltrexone 1 g ($2.8.10^{-3}$ mole) of 17-cyclopropylmethyl-4,5-epoxy 14-hydroxy 3-methoxy(5α)morphinan-6-one or methylnaltrexone, 8.1 g ($84.10^{-3}$ mole) of methanesulfonic acid and 0.63 g ($4.2.10^{-3}$ mole) of DL-methionine are mixed and the mixture is stirred for 8 hours at 40° C., then for 15 hours at 20° C. The reaction mixture is poured onto ice and ammonia is added until the pH=8 to 9. After extraction with ethyl acetate, the organic phases are washed with water, dried over sodiumsulfate and evaporated to dryness under reduced pressure.

0.77 g of crude naltrexone are thus obtained and the content is determined by liquid phase chromatography with an authentic sample as reference.

Content found: 82%.

Chemical yield of the dimethylation: 65.5%.

Thin layer chromatography: Rf=0.21 (toluene:acetone 7/3).

EXAMPLE 8

Preparation of 17-cyclobutylmethyl-4,5-epoxy-3,6,14-trihydroxy (5α,6α) morphinane or nalbuphine A mixture of 1 g ($2.71.10^{-3}$ mole) of 17-cyclobutylmethyl-4,5-epoxy-6, 14-dihydroxy 3-methoxy(5α,6α)- morphinane or methylnalbufine, 7.8 g ($81.10^{-3}$ mole) of methanesulfonic acid and 0.61 g ($4.1.10^{-3}$ mole) of DL-methionine is stirred for 8 hours at 40° C.

The reaction mixture is poured onto ice and ammonia is added until the pH=8 to 9. After extraction with ethyl acetate, the organic phases are washed with water, dried over sodium sulfate and evaporated to dryness under reduced pressure.

0.97 g of crude nalbuphine are thus obtained and the content is determined by liquid phase chromatography with an authentic sample as reference.

Content found: 47%.

Chemical yield of the demethylation: 47%.

Thin layer chromatography: Rf=0.50 (dichloromethane/methanol 85/15).

EXAMPLE 9

Preparation of naloxone

By using the same procedure of that described in Example 1, starting with 0.1 mole of N-allylnoroxycodone but varying the amounts of methanesulfonic acid and methionine and by modifying the temperature and the time of stirring of the reaction mixture, if necessary, the following results were obtained:

| Number of moles | | Temperature (°C.) | Time (h) | Yield of naloxone (%) | Unconverted starting material (%) |
|---|---|---|---|---|---|
| Methanesulfonic acid | Methionine | | | | |
| 3 | 0.15 | 20 | 55 | 66 | 23 |
| 3 | 0.15 | 40 | 15 | 70 | 5.6 |
| 3 | 0.15 | 40 | 40 | 58 | 0 |
| 3 | 0.15 | 40 / 60 | 4 / 3 | 67 | 4.6 |
| 3 | 0.15 | 60 | 14 | 58 | 1 |
| 3 | 0.15 | 80 | 4 | 53 | 1 |
| 4 | 0.15 | 40 | 13 | 68 | 3 |
| 4 | 0.30 | 40 | 9 | 61 | 1.5 |
| 5 | 0.15 | 40 | 11 | 64 | 2 |

EXAMPLE 10

Preparation of naloxone

A mixture of 1.7 g ($5.10^{-3}$ mole) of N-allylnoroxycodone, 11.25 g ($75.10^{-3}$ mole) of trifluoromethanesulfonic acid, 1.35 g ($75.10^{-3}$ mole) of water and 1.12 g ($7.5.10^{-3}$ mole) of DL-methionine is stirred for 21 hours at 20° C.

The mixture is made alkaline with ammonia until the pH=8 to 9, then is extracted with ethyl acetate. The product obtained is dissolved in chloroform, then treated with alumina and finally recrystallized from toluene.

1.23 g of naloxone are thus obtained, which represents a yield of 64%. The crystallization mother liquors still contain 1% of naloxone with respect to the starting material used.

We claim:

1. Process for the preparation of morphinane derivatives of formula:

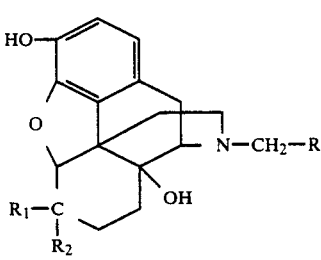

in which R is selected from hydrogen, $C_1$-$C_4$ alkyl, $C_3$-$C_4$ cycloalkyl, $C_2$-$C_4$ alkenyl or $C_2$-$C_4$ alkynyl, $R_1$ is hydrogen, $R_2$ is hydroxyl or $R_1$ and $R_2$ form together with the carbon atom to which they are attached the C=O group, as well as their pharmaceutically acceptable salts, wherein one equivalent of a morphine derivative of general formula:

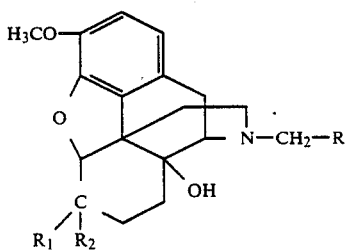

in which R, $R_1$ and $R_2$ are as defined previously, is reacted with 5 to 50 equivalents of a sulfonic acid selected from methanesulfonic acid and trifluoromethanesulfonic acid in the presence of 1 to 5 equivalents of a sulfide of general formula:

$$W-S-W_1 \qquad III$$

in which W and $W_1$, which are identical or different, each represents a $C_1$-$C_4$ linear alkyl radical, the group W being optionally substituted with one amino and one carboxyl or W and $W_1$ may form with the sulfur atom a saturated ring with up to 8 carbon atoms.

2. Process according to claim 1, wherein the reaction is carried out at a temperature between 20° and 60° C.

3. Process according to claim 1, wherein the temperature is between 30° and 40° C.

4. Process according to claim 1, wherein 25 to 35 equivalents of sulfonic acid are used.

5. Process according to claim 1, wherein 1 to 2 equivalents of sulfide of formula III are used.

6. Process according to claim 1, wherein the sulfide of formula III is di-n-butyl sulfide.

7. Process according to claim 1, wherein the sulfide of formula III is tetrahydrothiophene.

8. Process according to claim 1, wherein the sulfide of formula III is methionine.

9. Process according to claim 1, for the preparation of the compound of formula I in which R is vinyl and $CR_1R_2$ is a C=O group.

10. Process according to claim 1, for the preparation of the compound of formula I in which R is hydrogen and $CR_1R_2$ is a C=O group.

11. Process according to claim 1, for the preparation of the compound of formula I in which R is cyclopropyl and $CR_1R_2$ is a C=O group.

12. Process according to claim 1, for the preparation of the compound of formula I in which R is cyclobutyl, $R_1$ is hydrogen and $R_2$ is hydroxyl.

13. Process according to claim 2 wherein 25 to 35 equivalents of sulfonic acid are used.

14. Process according to claim 3, wherein 25 to 35 equivalents of sulfonic acid are used.

* * * * *